United States Patent
Larson (10) Patent No.: US 6,649,592 B1
(45) Date of Patent: Nov. 18, 2003

(54) PEPTIDE INHIBITORS OF LFA-1/ICAM-1 INTERACTION

(75) Inventor: Richard S. Larson, Albuquerque, NM (US)

(73) Assignee: Science & Technology Corporation @ UNM, Albuquerque, NM (US)

( * ) Notice: Subject to any disclaimer, the term of this patent is extended or adjusted under 35 U.S.C. 154(b) by 0 days.

(21) Appl. No.: 09/483,550

(22) Filed: Jan. 14, 2000

(51) Int. Cl.$^7$ ............................................... C07K 14/00
(52) U.S. Cl. .......................................... 514/9; 530/300
(58) Field of Search .................. 424/85.8; 435/252.1, 435/252.2, 252.3; 530/300, 350, 395; 514/9

(56) References Cited

U.S. PATENT DOCUMENTS

| | | | |
|---|---|---|---|
| 5,284,931 A | 2/1994 | Springer et al. | 424/85.8 |
| 5,612,216 A | 3/1997 | Springer et al. | 435/252.3 |
| 5,770,686 A | 6/1998 | Gallatin et al. | 530/300 |
| 5,831,036 A | 11/1998 | Springer et al. | 530/395 |

OTHER PUBLICATIONS

Tibbetts, et al., "Linear and cyclic LFA–1 and ICAM–1 peptides inhibit T cell adhesion and function," Peptides 21 (2000) 1161–67.

Gursoy, et al., "Structural recognition of an ICAM–1 peptide by its receptor on the surface of T cells: conformational studies of cyclo (1,12)–Pen–Pro–Arg–Gly–Gly–Ser–Val–Leu–Val–Thr–Gly–Cys–OH," J. Peptide Res., 53:4, 1999; 422–31.

WO 97/49731 A; "Cell adhesion inhibiting compounds," Dutta, et al.; Dec. 31, 1997.

International Search Report mailed May 25, 2001; International application No. PCT/US01/01382 filed Jan. 16, 2001.

Adgey, "An overview of the result of clinical trials with glycoprotein IIb/IIIa inhibitors," American Heart Journal, 135(4):S43–S55, 1998.

Jrad, et al., "Antigenicity of linear and cyclic peptides mimicking the disulfied loops in HIV–2 envelope glycoprotein: synthesis, reoxidation and purification," Journal of Peptide Research, 51:370–85, 1998.

Brown, et al., "All–trans retinoic acid regulates adhesion mechanism and transmigration of the acute promyelocytic leukaemia cell line NB-4 under physiologic flow," British Journal of Haematology, 107:86–98, 1999.

Budnik, et al., "Analysis of the production of soluble ICAM–1 molecules by human cells," Experimental Hematology, 24:352–59, 1996.

Cavazzana–Calvo, et al., "Prevention of bone marrow and cardia graft rejection in an H–2 haplotype disparate mouse combination by an anti–LFA–1 antibody," Transplantation, 59(11):1576–82, 1995.

Cosimi, et al., "In vivo effects of monoclonal antibody to ICAM–1 (CD54) in nonhuman primates with renal allografts," The Journal of Immunology, 144(12):4604–12, 1990.

Cumberbatch, et al., "Adhesion molecule expression by epidermal Langerhans cells and lymph node dendritic cells: a comparison," Arch Dermatol Res, 288:739–44, 1996.

Cuthbertson, et al., "Design of low molecular weight hematoregulatory agents from the structure—activity relationship of dimeric pentapeptide," J. Med. Chem., 40:2876–82, 1997.

Davis, et al., "Induction of persistent t cell hyporesponsiveness in vivo by monoclonal antibody to ICAM–1 in patients with rheumatoid arthritis," The Journal of Immunology, 154:3525–37, 1995.

DeMeester, et al., "Attenuation of rat lung isograft reperfusion injury with a combination of anti–ICAM–1 and anti–beta 2 integrin monoclonal antibodies," Transplantation, 62(10:1477–85, 1996.

Endemann, et al., "Novel anti–inflammatory compounds prevent CD11b/CD18, alpha M beta 2 (mac–1)–dependent neutrophil adhesion without blocking activation–induced changes in mac–1," The Journal of Pharmacology and Experimental Therapeutics, 276(1):5–12, 1996.

Fisher, et al., "Identification of the binding site in intercellular adhesion molecule 1 for its receptor, leukocyte function–associated antigen 1," Molecular Biology of the Cell, 8:501–15, 1997.

Goligorsky, et al., "Therapeutic effect of arginine–glycine–aspartic acid peptides in acute renal injury," Clinical and Experimental Pharmacology and Physiology, 25:276–79, 1998.

Gundel, et al., "The role of intercellular adhesion molecule–1 in chronic airway inflammation," Clinical and Experimental Allergy, 22:569–75, 1992.

Hasegawa, et al., "Prevention of autoimmune insulin–dependent diabetes in non–obese diabetic mice by anti–LFA–1 and anti–ICAM–1 mAb," International Immunology, 6(6):831–38, 1994.

Harning, et al., "Monoclonal antibodies to lymphocyte function–associated antigen–1 inhibit invasion of human lymphoma and metastasis of murine lumphoma," Clinical & Experimental Metastasis, 11(4):337–42, 1993.

Isobe, et al., "Specific acceptance of cardiac allograft after treatment with antibodies to ICAM–1 and LFA–1," Science, 255:1125–27, 1992.

(List continued on next page.)

Primary Examiner—Karen Cochrane Carlson
(74) Attorney, Agent, or Firm—Jagtiani + Guttag (57) ABSTRACT

Cyclic peptides inhibit LFA-1 interaction with ICAM-1 and are useful in treatment of hematopoietic neoplasms and in adjunct therapy in prevention of retinoic acid syndrome and diseases involving emigration of leukocytes into organ tissue.

30 Claims, 2 Drawing Sheets

OTHER PUBLICATIONS

Jackson, et al., "Potent alpha 4 beta 1 peptide antagonists as potential anti–inflammatory agents," J. Med Chem, 40:3359–68, 1997.

Jacobsson, et al., "Phase display shot–gun cloning of ligand–binding domains of prokaryotic receptors approaches 100% correct clones," BioTechniques 20:1070–81, 1996.

Jois, et al., "A Ca2+ binding cyclic peptide derived from the alpha–subunit of LFA–1: inhibitor of ICAM–1/LFA–1–mediated t–cell adhesion," J. Peptide Res., 53:18–29, 1999.

Kavanaugh, et al., "Treatment of refractory rheumatoid arthritis with a monoclonal antibody to intercellular adhesion molecule 1," Arthritis & Rheumatism, 37(7):992–99, 1994.

Ma, et al., "In vivo treatment with anti–ICAM–1 and anti–LFA–1 antibodies inhibits contact sensitization–induced migration of epidermal langerhans cells to regional lymph nodes," Cellular immunology, 158:389–99, 1994.

McMurray, "Adhesion Molecules in Autoimmune diesease," Seminars in Arthritis and Rheumatism, 25(4):215–33, 1996.

Murayama, et al., "Novel peptide ligands for integrin alpha 6 beta 1 selected from a phage display library," J. Biochem., 120:445–51, 1996.

Nakakura, et al., "Potent and effective prolongation by anti–LFA–1 monoclonal antibody monotherapy of non–primarily vascularized heart allograft survival in mice without t cell depletion," Transplantation, 55(2), 412–17, 1993.

Nakano, et al., "Efficacy of intraportal injection of anti–ICAM–1 monoclonal antibody against liver cell injury following warm ischemia in the Rat, The American Journal of Surgery," 170:64–66, 1995.

Noiri, et al., "Cyclic RGD peptides ameliorate ischemic acute renal failure in rats," Kidney International, 46:1050–58, 1994.

Ohman, et al., "Early clinical experience with integrelin, an inhibitor of the platelet glycoprotein IIb/IIIa integrin receptor," European Heart Journal, 16(Supp. L):50–55, 1995.

Ojima, et al., "Antithrombotic agents: from RGD to peptide mimetics," Bioorganic & Medicinal Chemistry, 3(4):337–60, 1995.

Picker, et al., "Physiological and molecular mechanisms of lymphocyte homing," Annu. Rev. Immunol. 10:561–91. 1992.

Servitje, et al., "Changes in T–cell phenotype and adhesion molecules expression in psoriatic lesions after low–dose cyclosporin therapy," Journal of Cutaneous Pathology, 23:431–36, 1996.

Brown, et al., "Development of cyclic peptide inhibitor of LFA–1 binding to ICAM–1," Blood 94 (Supplement):429a, 1999.

Suehiro, et al., "The ligand recognition specificity of beta 3 integrins," The Journal of Biological Chemistry, 271(17):10365–71, 1996.

Tibbetts, et al., "Peptides derived from ICAM–1 and LFA–1 modulate t cell adhesion and immune function in a mixed lymphocyte culture," Transplantation, 68(5):685–92, 1999.

Vanderslice, et al., "A cyclic hexapeptide is a potent antagonist of alpha 4 integrins," The Journal of Immunology, 158:1710–18, 1997.

Zhang, et al., "A discrete site modulates activation of I domains, The Journal of Biological Chemistry," 271(47):29953–57, 1996.

Welply, et al., "A peptide isolated by phage display binds to ICAM–1 and inhibits binding to LFA–1," Proteins: Structure, Function, and Genetics, 26:262–70, 1996.

Winter, et al., "Combinatorial effects of LFA–1 dependent stromal cell adhesion and soluble factors on t–cell leukemia cell line survival," Blood 89 (Supp. 1):81a, 1998.

SEQUENCE LISTING

<160> NUMBER OF SEQ ID NOS: 33

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 1

Cys Leu Leu Arg Met Arg Ser Arg Cys
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 2

Cys Leu Leu Arg Met Arg Leu Ile Cys
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 3

Cys Leu Leu Arg Met Arg Ser Ile Cys
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 4

Cys Leu Leu Arg Met Arg Leu Arg Cys
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 5

Cys Leu Leu Arg Pro Arg Ser Ile Cys
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 6

-continued

```
Cys Leu Leu Arg Pro Arg Ser Arg Cys
  1               5
```

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 7

```
Cys Leu Leu Arg Pro Arg Leu Ile Cys
  1               5
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 8

```
Cys Leu Leu Arg Pro Arg Leu Arg Cys
  1               5
```

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 9

```
Cys Leu Leu Arg Met Asn Ser Ile Cys
  1               5
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 10

```
Cys Leu Leu Arg Met Asn Ser Arg Cys
  1               5
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 11

```
Cys Leu Leu Arg Met Asn Leu Ile Cys
  1               5
```

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 12

```
Cys Leu Leu Arg Met Asn Leu Arg Cys
```

```
<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 13

Cys Leu Leu Arg Pro Asn Ser Ile Cys
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 14

Cys Leu Leu Arg Pro Asn Ser Arg Cys
 1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 15

Cys Leu Leu Arg Pro Asn Leu Ile Cys
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 16

Cys Leu Leu Arg Pro Asn Leu Arg Cys
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 17

Cys Met Leu Arg Met Arg Ser Ile Cys
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 18

Cys Met Leu Arg Met Arg Ser Arg Cys
 1               5
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 19

Cys Met Leu Arg Met Arg Leu Ile Cys
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 20

Cys Met Leu Arg Met Arg Leu Arg Cys
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 21

Cys Met Leu Arg Pro Arg Ser Ile Cys
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 22

Cys Met Leu Arg Pro Arg Ser Arg Cys
 1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 23

Cys Met Leu Arg Pro Arg Leu Ile Cys
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 24

Cys Met Leu Arg Pro Arg Leu Arg Cys
 1               5

```
<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 25

Cys Met Leu Arg Met Asn Ser Ile Cys
 1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 26

Cys Met Leu Arg Met Asn Ser Arg Cys
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 27

Cys Met Leu Arg Met Asn Leu Ile Cys
 1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 28

Cys Met Leu Arg Met Asn Leu Arg Cys
 1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 29

Cys Met Leu Arg Pro Asn Ser Ile Cys
 1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 30

Cys Met Leu Arg Pro Asn Ser Arg Cys
 1               5
```

-continued

```
<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 31

Cys Met Leu Arg Pro Asn Leu Ile Cys
  1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 32

Cys Met Leu Arg Pro Asn Leu Arg Cys
  1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 33

Cys Leu Met Ile Arg Met Leu Arg Cys
  1               5
```

PEPTIDE INHIBITORS OF LFA-1/ICAM-1 INTERACTION

BACKGROUND

1. Field of the Invention

The present invention relates to the field of biologically active peptide containing compositions for use in the prevention and treatment of hematopoietic neoplastic diseases, particularly leukemia.

2. Description of Related Art

LFA-1 (lymphocyte function associated antigen-1) is an integrin αβ heterodimer (Carlos and Harlan, 1994; Springer, 1994; Larson and Springer, 1990; McEver, 1990; Picker and Butcher, 1992). Although three other integrins restricted in expression to leukocytes share the same β subunit and have homologous α subunits (Mac-1, p150,95, and alpha d), only LFA-1 is expressed on normal and leukemia T cells (Larson and Springer, 1990). LFA-1 binds ICAM-1 (intracellular adhesion molecule), and although LFA-1 is constitutively expressed on all leukocytes, LFA-1 binding to ICAM-1 requires cellular activation. Activation, in part, results in conformational changes in LFA-1 that affect its avidity for ICAM-1. In contrast, ICAM-1 is constitutively avid and expressed on a wide array of cell types including leukocytes, endothelium, stromal cells, and fibroblasts. In a model developed by the present inventor, a stromal cell derived soluble factor cooperates with LFA-1 on the surface of T lineage acute lymphoblastic leukemia (T-ALL) cells (Winter et al., 1998). The LFA-1 on T-ALL cells results in bone marrow (BM) stromal cell binding via ICAM-1 that leads to enhanced leukemia cell survival. Furthermore, aberrant LFA-1/ICAM-1 dependent interaction between circulating leukemia cells and endothelial cells lining blood vessels promotes extravasation of leukemia cells into tissue as seen in the life-threatening therapeutic complication of acute leukemia, retinoic acid syndrome (Brown et al., 1999). Hence, the development of effective in vivo inhibitors of LFA-1/ICAM interaction would be useful in the therapy of acute leukemia and prevention of therapeutic complications.

The present inventor has shown, for example, that inhibition of LFA-1/ICAM-1 dependent stromal cell binding with mAbs decreases survival of T-ALL cell lines and T-ALL cells isolated from patients. In one study, a representative sample from a patient with T-ALL showed that survival of T-ALL cells is augmented by BM stromal cells and that survival is inhibited by mAbs directed against LFA-1 (mAb TSI/22,5 µg/ml) or its ligand ICAM-1 (mAb 84H10, 10 µg/ml). This observation has been replicated for T-ALL cell lines Jurkat and Sup TI as well as a subset of patients with T-ALL. However, even though in vivo use of mAbs against LFA-1 or ICAM-1 blocks LFA-1 function in a number of disease models, unfortunately anaphylactic reactions and secondary physiologic effects have hampered this approach (McMuray, 1996; DeMeester: et al., 1996; Jackson et al., 1997; Cuthbertson et al., 1997; Gundel et al., 1992; Haming et al., 1993; Nakano et al., 1995).

Another means to interfere with protein-protein interactions is through the use of small peptide inhibitors. In fact, small peptide inhibitors to adhesion molecules structurally-related to LFA-1 have recently been approved for clinical use in coagulopathies (Ohman et al., 1995; Adgey et al., 1998; Leficovis and Topol, 1995). Short linear peptides (<30 amino acids) have also been described that prevent or interfere with integrin dependent firm adhesion using sequences derived from integrin or their ligands. In particular, these peptides have been derived from a number of integrin receptors: the β2 and β3 subunits of integrins, and the $\alpha_{iib}$ subunit of ICAM-1, and VCAM-1 (Murayama et al., 1996; Jacobsson and Frykberg, 1996; Zhang and Plow, 1996; Budnik et al., 1996; Vanderslice et al, 1997; Suehiro et al., 1996; Endemann et al., 1996). However, the clinical applicability of these linear peptides is limited. The half maximal inhibitory concentration (IC$_{50}$; concentration at which aggregation is inhibited 50%) for most of these peptides is $10^{-4}$ M with purified receptor-ligand pairs (univalent interactions) and they are ineffective at inhibiting multivalent interactions, during cell-cell adhesion. In addition, linear peptides have short serum half-lives because of proteolysis. Therefore, prohibitively high concentrations of peptide would have to be administered in a clinical setting and a biologic effect would not necessarily occur.

Longer peptides, ranging in length from 25–200 residues, have also been reported to block β1, β2, and β3 integrin dependent adhesion (Zhang and Plow, 1996; Budnik et al., 1996; Vanderslice et al, 1997; Suehiro et al., 1996; Endeman et al., 1996). In general, these peptide inhibitors may have higher affinities or slower off-rates than short peptides and, therefore, are better inhibitors. However, they are still susceptible to proteolysis.

Therefore, a need exists to develop novel and specific classes of pharmaceutical agents to inhibit the binding of LFA-1 and ICAM-1 and to be useful in the treatment of hematopoietic neoplastic diseases as well as other diseases that involve emigration of leukocytes from blood into tissue, such as myocardial infarction, radiation injury, asthma, rheumatoid arthritis, and lymphoma metastasis.

SUMMARY

The present invention addresses the problems in the art by providing compositions that include cyclic peptide inhibitors of binding interactions between the integrin, lymphocyte function associated antigen-1 (LFA-1) expressed on leukocytes, including leukemic T-cells, and intracellular adhesion molecule 1 (ICAM-1), expressed on a variety of cell types. As stated above, this binding of activated LFA-1 is implicated in a variety of diseases and inhibition of this binding interaction with a cyclic peptide inhibitor will have implications in the treatment or management of those diseases.

The present invention may be described, therefore, in certain aspects as a composition comprising a cyclic peptide inhibitor of LFA-1/ICAM-1 interaction, wherein the composition has the amino acid sequence, CLLRMRSIC (SEQ ID NO:3) or a conservative variant thereof. Conservative variants are described elsewhere herein, and include the exchange of an amino acid for another of like charge, size, or hydrophobicity, for example. The present disclosure also include variants of the sequence disclosed above in which the 3$^{rd}$ and 4$^{th}$ amino acids remain the same and other amino acids of the sequence are substituted and tested empirically for their ability to inhibit the LFA-1/ICAM-1 interaction. The amino acid sequence is numbered in the conventional sense, in that the first amino acid on the N-terminus is cysteine, followed by 7 amino acids and then a carboxy-terminal cysteine. In the practice of the invention, the two terminal cysteines may form a disulfide bonded cystine residue resulting in a cyclic peptide as is well known in the art.

Based on the empirical data obtained by the inventor and disclosed herein, a cyclic peptide of the invention may have the sequence of SEQ ID NO:3, or it may be a derivative of that sequence in which the second amino acid is methionine (SEQ ID NO:17), or in which the 5$^{th}$ amino acid is proline (SEQ ID NO:5), or in which the 6$^{th}$ amino acid is asparagines (SEQ ID NO:9), or in which the 7$^{th}$ amino acid is leucine (SEQ ID NO:2), or in which the 8$^{th}$ amino acid is arginine (SEQ ID NO:1), or any combination of these substitutions, or even conservative variants of any of these substitutions. In the preferred embodiments of the invention, the peptides or peptide mimetics of the invention exhibit an inhibition constant (IC$_{50}$) for the binding interaction of LFA-1/ICAM-1 of from about 10 $\mu$M to about 900 $\mu$M for cell aggregation or from about 10 to about 250 nM for monovalent LFA-1/ICAM-1 binding. The term "IC$_{50}$" is well known in the art, and means the half maximal inhibitory concentration, or concentration at which aggregation is inhibited by 50%.

Any of the compositions described herein may be formulated for pharmacological or therapeutic administration either to a mammal, or more preferably to a human. As such, the compositions may be contained in a pharmaceutically acceptable carrier. The preferred mode of administration of a peptide active agent is by injection, either intravenous, intra-arterial, intramuscular or subcutaneous. Other routes of administration may also be possible and would be included within the scope of the present disclosure.

The compositions may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be suitably fluid. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

A peptide can be formulated into a composition in a neutral or salt form. Pharmaceutically acceptable salts, include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

It is an aspect of the present disclosure that the disclosed compositions may be used in adjunct therapy in standard treatments for diseases such as hematopoietic neoplasms. The present invention may be described therefore, in certain embodiments as a method of preventing retinoic acid syndrome in a subject receiving all-trans retinoic acid, comprising administering to the subject an effective amount of a composition comprising a cyclic peptide, wherein the peptide has the amino acid sequence CLLRMRSIC, SEQ ID NO:3, or a conservative variant thereof.

An embodiment of the invention may also be described as a method for inhibiting growth of leukemia cells comprising preventing an LFA-1/ICAM-1 interaction between the leukemia cells and support cells such as bone marrow stromal cells, wherein the method comprises contacting the leukemia cells with a cyclic peptide inhibitor of the LFA-1/ICAM-1 interaction, and further wherein the amino acid sequence of the cyclic peptide inhibitor is not a fragment of the amino acid sequence of LFA-1 or ICAM-1. In the practice of this method, the leukemia cells are preferably in a leukemia patient and contacting comprises administering the cyclic peptide to the patient.

An embodiment of the invention is also a therapeutic package for dispensing to, or for use in dispensing to, a mammal or human being treated for a hematopoietic neoplastic disease, myocardial infarction, radiation injury, asthma, rheumatoid arthritis, or lymphoma metastasis, wherein the package contains in a unit dose, an amount of a cyclic peptide having the amino acid sequence CLLRMRSIC, SEQ ID NO:3, or a conservative variant thereof, effective to inhibit an LFA-1/ICAM-1 interaction in a subject when administered periodically. In certain embodiments a unit dose is from about 10 to about 500 µg/Kg, or is from about 50 to about 250 µg/Kg, or from about 120 to about 150 µg/Kg. The unit dose may be an initial bolus dose which may be followed by a continuous infusion of about 5 to about 250 µg/K/min, or from about 40 to about 60 µg/K/min, or may be about 50 µg/K/min. Alternatively, unit doses may be repeated daily, and administered multiple times per day. Dosage regimens are not limited to those exemplified, and the invention encompasses any dosage regimen that delivers a therapeutically effective dose. An example of clinical administration of a peptidomimetic inhibiting an integrin function is documented by Ohman et al. (1995).

An embodiment of the present disclosure is a method of inhibiting emigration of leukocytes from blood into tissue in a subject comprising administering to the subject an amount of a cyclic peptide having the amino acid sequence, CLLRMRSIC, SEQ ID NO:3, or a conservative variant thereof, effective to inhibit an LFA-1/ICAM-1 interaction in the subject. In preferred embodiments the subject is susceptible to the development of, or is suffering from a hematopoietic neoplastic disease, myocardial infarction, radiation injury, asthma, rheumatoid arthritis, or lymphoma metastasis.

A further embodiment of the invention is a method comprising a competitive binding assay for screening the ability of candidate compounds to bind to ICAM-1. The method comprises assessing the displacement by candidate compounds CLLRMRSIC, SEQ ID NO:3, or a conservative variant thereof, bound to ICAM-1.

Other embodiments of the present disclosure include methods of therapy relating to tissue allografts such as renal, heart and thryoid allografts, bone marrow transplants, diabetes, rheumatoid arthritis, psoriasis, T-cell mediated sensitization reactions such as contact sensitization, and other T-cell mediated disorders. Such methods comprise administering to the subject an amount of a cyclic peptide having the amino acid sequence, CLLRMRSIC, SEQ ID NO:3, or a conservative variant thereof, effective to inhibit an LFA-1/ICAM-1 interaction in the subject.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Hematopoietic neoplasms including acute leukemia constitute 7% of male and 6% of female cancer (Ries et al., 1994). If untreated, the clinical course of acute leukemia is rapidly fatal. Drugs to treat acute leukemia usually interfere with cell replication, and as a result, these drugs have non-specific physiologic consequences and undesirable side effects. One of the fundamental problems in the development of novel leukemia therapies is the identification of pharmaceutical targets and the production of pharmaceutical agents against those targets. The present inventor has shown that LFA-1 and ICAM-1 are molecular targets for use in the therapy of acute leukemia using two assays that recapitulate the molecular and cellular events leading to leukemia cell proliferation in the marrow and spread of leukemia cells to distant sites. The first assay simulates the marrow microenvironment. In this assay, T lineage acute lymphoblastic leukemia (T-ALL) cells isolated from patients are co-cultured with bone marrow (BM) stromal cells that support hematopoiesis. T-ALL cells isolated from patients will die in ex vivo culture, and BM stromal cells have been shown to support ex vivo survival of T-ALL cells. Furthermore, in co-culture experiments mAbs to LFA-1 and ICAM-1 dramatically decrease T-ALL cell survival by inhibiting adherence to bone marrow stromal cells. This latter finding indicates that survival of T-ALL cells in the marrow microenvironment is dependent on proper LFA-1/ICAM-1 binding. Since failure to eradicate leukemia cells in the marrow is a major reason for treatment failure, adjunct therapy that included inhibition of LFA-1/ICAM-1 ligation between leukemia cells and T-ALL cells may cause T-ALL cell death and improved patient outcome. This may have applicability to all T-cell leukemias.

The present inventor has also established a model and dissected the mechanism of a life-threatening therapeutic complication of acute promyelocytic leukemia (APL), retinoic acid syndrome. All-trans retinoic acid (ATRA) promotes a complete remission in up to 80% of patients with APL. However, retinoic acid syndrome occurs in up to 30% of patients and is caused by APL cells infiltrating organs after retinoic acid therapy. Using an apparatus known as a parallel plate flow chamber, the interactions that occur in blood vessels between circulating leukemia cells and endothelial cells have been recapitulated under physiologic flow conditions (Brown et al., in press; Larson et al;, 1997). Upregulation of LFA-1 activity on APL cells after retinoic acid treatment results in APL cell binding to and transmigration through endothelium, analogous to the organ infiltration seen in APL patients being treated with retinoic acid. mAbs against LFA-1 and ICAM-1 completely inhibit the binding to and transmigration through endothelium. Hence, inhibition of LFA-1/ICAM interaction in patients with APL being treated with retinoic acid may protect against the development of retinoic acid syndrome. LFA-1/ICAM inhibition is also applicable to the use of alternatives to retinoic acid, such as 9-cis-retinoic acid or various synthetic retinoids, in APL treatment, to the extent that they cause retinoic acid syndrome.

Inhibition of the LFA-1 and ICAM-1 binding has potential therapeutic benefits relating to blocking allograft rejection allografts, including cardiac, renal and thryoid allografts (Isobe et al., 1992; Stepkowski et al., 1994; Cosimi et al., 1990; Nakakura et al., 1993; Talento et al., 1993), bone marrow transplants (Tibbetts et al., 1999; Cavazzana-Calvo et al., 1995) T-cell mediated sensitization reactions (Ma et al., 1994; Cumberbatch et al., 1992), diabetes (Hasegawa et al., 1994) and rheumatoid arthritis (Davis et al., 1995; Kavanaugh et al., 1994). Expression of ICAM-1 by keratinocytes is also implicated in the etiology of psoriasis, and inhibition of LFA-1/ICAM-1 binding presents a possible point of therapeutic intervention (Servitje et al., 1996). Thus the peptide compositions of the present invention may be used in treatment of the above conditions and more generally in any condition T-cell mediated condition wherein T-cells are activated via interaction of LFA-1 and ICAM-1.

The present disclosure provides novel peptide containing compositions that inhibit the LFA-1/ICAM-1 interaction. Preferred are compositions including nine amino acid peptides in which the terminal amino acids are cysteines, thus allowing the peptide to exist in a cyclic form by disulfide bonding between the terminal amino acids. Cyclizing small peptides through disulfide bonds between the N- and C-terminus cysteines may circumvent problems of affinity and half-life. Disulfide bonds connecting the amino and carboxy terminus prevent proteolysis and increasing the rigidity of the structure may yield higher affinity compounds. Cyclic peptides may also have longer half-lives in serum (Picker and Butcher, 1992). Moreover, the side-effects from peptide therapy are minimal, since anaphylaxis and immune responses against the small peptide occur only rarely (Ohman et al., 1995; Adgey, 1998). Finally cyclic peptides have been shown to be effective inhibitors in vivo of integrins involved in human and animal disease (Jackson et al., 1997; Cuthbertson et al., 1997; Leficovis and Topol, 1995; Goligorsky et al., 1998; Ojima et al., 1995; Noiri et al., 1994).

The present invention is not limited to peptides cyclized by oxidation of terminal cysteine residues. Cyclic peptides can be prepared by alternative methods, such as incorporation of a type II' β-turn dipeptide (Doyle et al., 1996). Other examples of cyclization methods are discussed and disclosed in U.S. Pat. No. 6,008,058, herein incorporated in entirety by reference. Thus, embodiments of the present invention include cyclic peptides comprising residues 2 through 8 of the consensus sequence shown in Table 1, and variants thereof, wherein the cyclic structure is achieved by any suitable method of synthesis.

Figure 2:
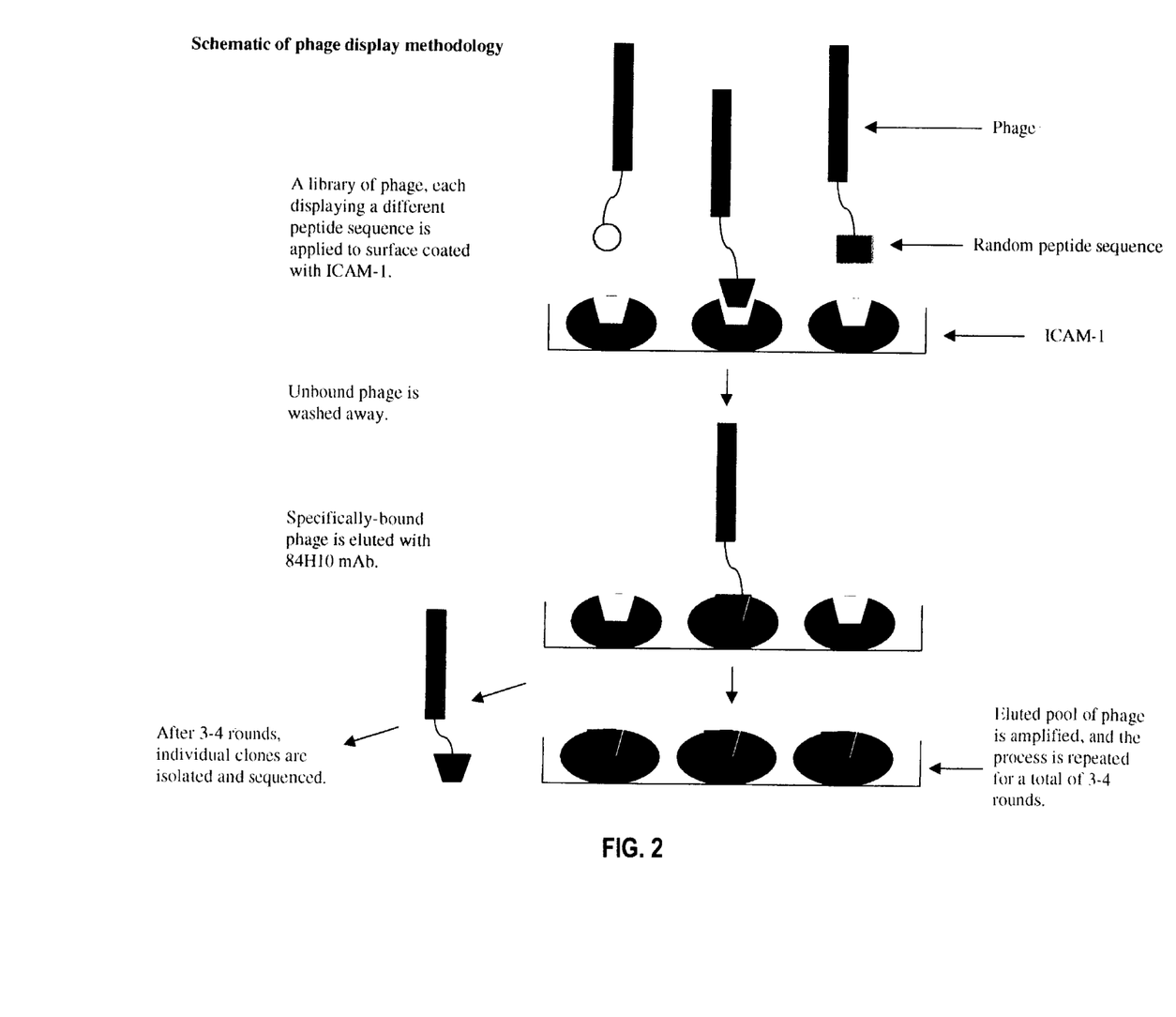
FIG. 2 is a schematic of the phage display methodology wherein a phage library with random peptide sequences is screened for ability to bind to purified ICAM-1.

As a part of the present disclosure, phage display has been used to identify peptide sequences that bind ICAM-1 and block LFA-1/ICAM interaction. Briefly a library of phage was screened for its ability to bind the LFA-1 ligand, ICAM-1. Human ICAM-1 has been previously isolated in functional form (Larson et al., 1990), and a variation of this technique was used to obtain purified recombinant soluble ICAM-1 for use in phage display. Each phage in the library has the potential to display a unique cyclic heptapeptide fused to its gene III coat on its surface. The linkage of the displayed random peptide with a phage surface protein forms the basis of the technique. The library consists of approximately $2.8 \times 10^9$ random heptapeptide sequences expressed on phage, compared to $20^7$ (20 possible amino acids in 7 different positions) or $1.28 \times 10^9$ possible heptapeptide sequences. The phage were then screened for their ability to bind purified ICAM-1 by interaction with the displayed heptapeptide sequences. The phage were then screened for their ability to bind purified ICAM-1 by panning (FIG. 2). Bound phage is eluted using the anti-ICAM-1 mAb RR1/1. This mAb binds to amino acid residues on ICAM-1 that are similar to those to which LFA-1 binds (Staunton et al., 1990). Elution with R6.5 allowed for isolation of phage expressing cyclic peptides that bind a region on ICAM-1 that is shared with LFA-1 binding. In addition, phage were eluted with mAb for 1 hour so that the peptides with highest affinity and slower off-rates (i.e., peptides most likely to be potent in vivo inhibitors) would be included. Thus, peptide sequences that block ICAM-1/LFA-1 interactions are identified.

Adherent phage were selected and amplified through four rounds of panning. The sequences of 12–18 phage in each round were determined. A working consensus peptide was determined after nucleotide sequencing of 18 phage in the fourth and final round (Table 1). Amino acids that were recurring but occurred at lower frequency and did not fit into the consensus sequence are also shown below. The recurring amino acids form the basis of derivative structures. The ability of each phage isolated after four rounds of panning to specifically bind ICAM-1 was also determined in an ELISA assay with serial dilutions of phage.

TABLE 1.

Peptide Sequences Expressed on Phage that Bind ICAM-1

| Amino acid position | 1 | 2 | 3 | 4 | 5 | 6 | 7 | 8 | 9 |
|---|---|---|---|---|---|---|---|---|---|
| Consensus* (SEQ ID NO: 3) | C | L | L | R | M | R | S | I | C |
| Recurring amino acids |   | M |   |   | P | N | L | R |   |

The following techniques have been developed or modified for use in the present examples described below.

Rapid Aggregation Assay for Screening Peptide Effectiveness.

LFA-1 dependent cell aggregation has been previously studied using an aggregation assay with a variety of leukocyte subclasses and cell lines (Larson et al., 1990; Wang et al., 1988; Larson et al., 1997). In the present studies, JY cells are placed in a 96 well plate with an appropriate stimulus to induce cell aggregation. MAbs and other small compounds such as peptides may be added in order to determine their effect on cell aggregation. The concentration of the compound added to the wells and the degree of aggregation may be quantified.

Assay for Measuring LFA-1 Dependent ex vivo Survival of Leukemic Cells.

A co-culture assay for quantifying ex vivo T-ALL cell survival on bone marrow derived cell stromal cells has been developed. Leukemic cell survival in this assay is dependent on proper LFA-1/ICAM-1 interaction (Winter et al., 1998).

Parallel Plate Flow Chamber for Measuring Leukocyte-endothelial Cell Interaction Under Physiologic Flow Conditions in vivo.

A parallel plate flow chamber containing endothelial cell on layers permits accurate recapitulation of leukocyte extravasation. This technique has been used to evaluate attachment and transmigration of leukemic cells to human umbilical vein endothelial cells. That work has lead to a proposed mechanism for retinoic acid syndrome, a life-threatening complication of leukemia therapy, as described hereinabove (Brown et al., 1997).

Monoclonal Antibodies

In order to have adequate monoclonal antibodies at a reasonable cost, hybridomas were grown by the present inventor and mAbs were purified for blocking studies. The following monoclonal antibodies have been isolated from hybridoma supernatants: mAbs against LFA-1 (TS2/4 and TSI/22) and ICAM-1 (RRI/1, R6.5 and 84H10) (Larson et al., 1997).

Screening Assay

The ability of candidate compounds to bind to ICAM-1 is assessed by a competitive binding assay. Candidate compounds may be peptide or non-peptide compounds. Binding to ICAM-1 is quantified by the ability to displace CLLRMRSIC (SEQ ID NO:3) or a conservative variant thereof, from ICAM-1. Displaced CLLRMRSIC (SEQ ID NO:3) or a conservative variant thereof, can be assayed by a number of techniques. For example, radiolabeled peptide can be synthesized using commercially available radiolabeled amino acids precursors. Peptides radiolabelled with $H^3$, $C^{14}$ or $S^{35}$ can be quantified by routine liquid scintillation techniques. Alternatively, a fluorescent labeled peptide can be synthesized. For example, lysine can be inserted in a non-critical position and labeled with fluoescein isothiocyanate ("FITC"). In addition to FITC, the peptide may be labeled with any suitable flurophore. Separation of bound from unbound peptide and quantitation of displaced peptide can be performed by routine techniques known to one of skill in the art. This embodiment of the invention is not limited by the method used to quantify the displaced peptide, and any suitable analytical technique may be used and be within the scope of the invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Consensus Sequence Peptide Blocks LFA-1/1CAM-1 Dependent Cell Aggregation

Figure 1:
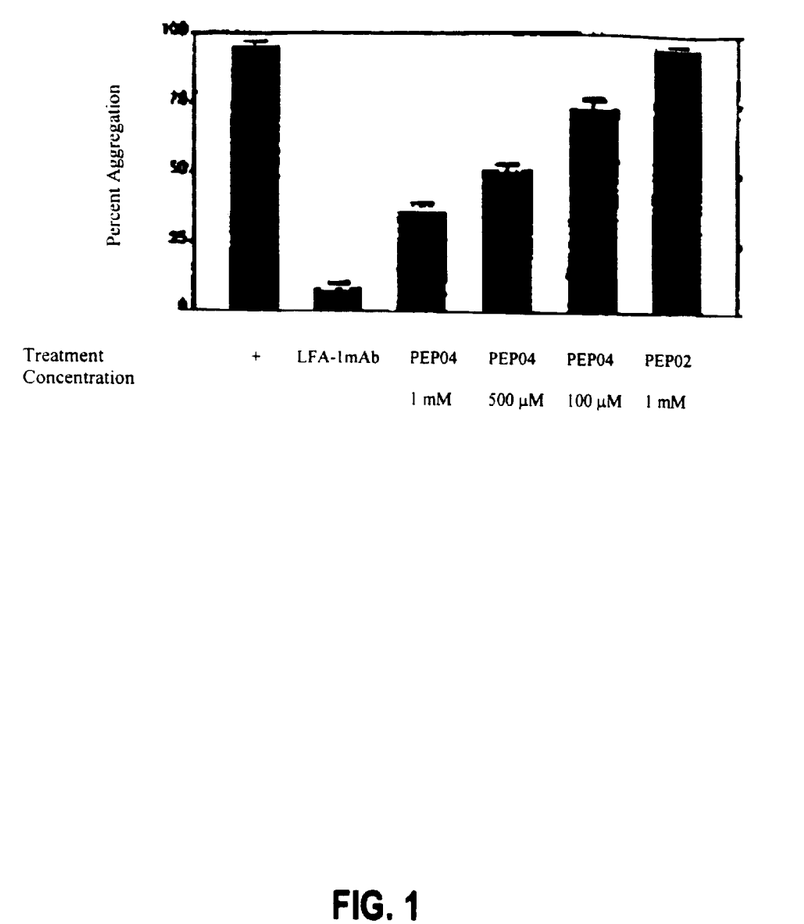
FIG. 1 is a bar graph display of data showing aggregartion of JY cells being inhibited by either mAbs against LFA-1, or by titration of 100 µM to 1 mM of the consensus peptide (SEQ ID NO:3) disclosed in Table 1 (designated PEP04). A randomized peptide, CLMIRMLRC (SEQ ID NO:33, designated PEP02) at a concentration of 1 mM is shown to be ineffective.

The consensus peptide from Table 1 was synthesized and tested in a screening assay for its ability to inhibit aggregation of the cell line JY, which aggregates in an LFA-1/CAM-1 dependent manner. Aggregation measurements are relatively rapid (1 hour) and quantifiable. Furthermore, small volumes are used (150 µl) minimizing peptide consumption. Finally, cell aggregation in vitro depends on a multivalent LFA-1/ICAM-1 interaction. A peptide that is identified as being able to block cell aggregation in vitro is, therefore, likely to have affinity and off-rate characteristics that would make it an effective in vivo inhibitor, since cell-cell interaction in vivo also involves multivalent LFA-1/ICAM-1 interaction. Using this assay, the consensus peptide sequence has an $IC_{50}$ of 500 µM (FIG. 1).

EXAMPLE 2

Identification of Derivative Peptide Antagonists

The consensus peptide sequence (SEQ ID NO:3) identified by phage display and described in Example 1 has an $IC_{50}$ of 900 µM for cell aggregation and 250 nM for monovalent LFA-1/ICAM-1 binding. For in vivo use, preferred peptides would have $IC^{50}$'s of about 10 µM to about 800 µM for cell aggregation and from about 10 to 250 nM for monovalent LFA-1/ICAM-1 binding. In order to obtain more effective inhibitory peptides, standard techniques of designing derivative structures may be used to produce candidates to be tested for enhanced inhibitory capacity. This strategy has been shown to be effective in developing in vivo peptide inhibitors to other adhesion molecules (Ohman et al., 1995; Adgey, 1998).

For example, heptapeptide sequences are proposed on the basis of the observed consensus sequence of different phage sequences that were discovered in the phage display studies described above. Two of the amino acid positions in the consensus sequence show greater than 80% identity among phage and therefore are fixed (positions 3 and 4 of Table 1). The other positions are altered using 1 of 2 possible amino acids as shown in Table 2. The amino acids employed in the altered positions are identical to the recurring amino acids identified by phage display, but are represented at too low a frequency to be incorporated in the consensus sequence peptide. Using these combinations, 32 cysteine restrained heptapeptides are available as candidate inhibitors.

Peptides are initially tested for their ability to block LFA-1/ICAM dependent aggregation of the cell line JY (Wang et al., 1988; Larson et al., 1997). Peptides are preferably tested over a range of concentrations ($10^1$ to $10^8$ µM, for example) and the concentration leading to half maximal inhibition of aggregation (IC50) is determined for all the peptide sequences.

TABLE 2

Hypothetical Peptide Antagonists

| No. | Sequence |
| --- | --- |
| SEQ ID NO: 3 | CLLRMRSIC |
| SEQ ID NO: 1 | CLLRMRSRC |
| SEQ ID NO: 2 | CLLRMRLIC |
| SEQ ID NO: 4 | CLLRMRLRC |
| SEQ ID NO: 5 | CLLRPRSIC |
| SEQ ID NO: 6 | CLLRPRSRC |
| SEQ ID NO: 7 | CLLRPRLIC |
| SEQ ID NO: 8 | CLLRPRLRC |
| SEQ ID NO: 9 | CLLRMNSIC |
| SEQ ID NO: 10 | CLLRMNSRC |
| SEQ ID NO: 11 | CLLRMNLIC |
| SEQ ID NO: 12 | CLLRMNLRC |
| SEQ ID NO: 13 | CLLRPNSIC |
| SEQ ID NO: 14 | CLLRPNSRC |
| SEQ ID NO: 15 | CLLRPNLIC |
| SEQ ID NO: 16 | CLLRPNLRC |
| SEQ ID NO: 17 | CMLRMRSIC |
| SEQ ID NO: 18 | CMLRMRSRC |
| SEQ ID NO: 19 | CMLRMRLIC |
| SEQ ID NO: 20 | CMLRMRLRC |
| SEQ ID NO: 21 | CMLRPRSIC |
| SEQ ID NO: 22 | CMLRPRSRC |
| SEQ ID NO: 23 | CMLRPRLIC |
| SEQ ID NO: 24 | CMLRPRLRC |
| SEQ ID NO: 25 | CMLRMNSIC |
| SEQ ID NO: 26 | CMLRMNSRC |
| SEQ ID NO: 27 | CMLRMNLIC |
| SEQ ID NO: 28 | CMLRMNLRC |
| SEQ ID NO: 29 | CMLRPNSIC |
| SEQ ID NO: 30 | CMLRPNSRC |
| SEQ ID NO: 31 | CMLRPNLIC |
| SEQ ID NO: 32 | CMLRPNLRC |

EXAMPLE 3

An alternative derivative peptide strategy is to subject the consensus sequence peptide to an alanine-screening procedure as described by Cunningham and Wells, 1989. Alanine will be separately introduced into each position to identify specific side chains in the peptide that modulate binding to ICAM. Once identifed, such amino acids are exchanged for conservative amino acid substitutions. Such substitutions are of amino acids of like charge, e.g., as described by Dayoff et al., Atlas of Protein Sequence and Structure; vol 5, Suppl. 3, pp3,45–362 (M. O. Dayoff, ed., Nat'l BioMed Research Fdn., Washington, D.C. 1979). An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as conservative variants. This type of derivative strategy has also been successful at identifying higher affinity peptides (Ohman et al., 1995; Adgey, 1998). In addition to binding to ICAM, conservative varaints can also be screened for other desirable properties such as a longer serum-half life or desirable other pharmacokinetic of pharmacodymanic properties.

EXAMPLE 4

Identification of Peptide Inhibitors of LFA-1/ICAM-1 Interaction

A co-culture assay has been developed by the present inventor that quantifies ex vivo survival of T-ALL cells (Winter et al., 1998). Using this assay, survival of T-ALL cell lines as well as T-ALL cells isolated from patients required LFA-1 binding to ICAM-1 on bone marrow (BM) derived stromal cells. In this assay cryopreserved or fresh leukemic samples are seeded onto HS5 stromal cell monolayers in 24 well plates. The stromal cell line HS5 has been previously shown to support complete hematopoiesis of normal precursor cells (Roecklein and Torak-Storb, 1995). HS5 cells are γ-irradiated with 2500 cGy, a dose that has been determined to prevent stromal cell proliferation over 168 hours. Leukemia cells are harvested at 1 and 96 hours. The number of leukemic cells recovered is measured in a flow cytometer by techniques based on those known in the art (Manabe et al., 1992; Manabe et al., 1994). The leukemia cells are stained by direct immunofluorescence using a fluoroisothiocyanate (FITC) labeled mAb directed against a pan T-ALL antigen CD5 as described (Larson et al., Leukocyte Typing, 1990; Larson and McCurley, 1995). A gate is set around the area of light scatter where the viable CD5 positive T-ALL cells are found at the beginning of the cultures. Then, the T-ALL cells with predetermined light scattering and CD5 presentation are enumerated by counting the number of events passing through the gate in a 60 second time period. In each analysis $5 \times 10^5$ fluorescent Immuno-Chek beads (Coulter, Hialeah, Fla.) are added to each sample. The number of beads that pass through the flow cytometer in 60 seconds is also counted, allowing the measured bead number to serve as an internal control for the volume that passes through the flow cytometer in 60 seconds. The calculation is as follows: (number of CD5 T-ALL cells/volume passed through flow cytometer as determined by fluorescent beads) X volume of the sample=the number of cells in the sample. The percentage of survival is calculated by: (number of cells in test sample at t-96 h/number of cell in sample at t-1 h)×100.

An additional assay has been developed that provides an in vitro model of APL cells binding to activated endothelium, and that recapitulates events that occur in retinoic acid syndrome using a parallel plate flow chamber (Larson et al., 1997; Brown et al., 1999)). A parallel plate flow chamber simulates the physiologic flow conditions in blood and adhesive interactions in post-capillary venules. Post-capillary venules are the physiologically relevant locations of leukemia cell-endothelial cell interaction and extravasation. Since parallel plate flow chamber experiments have been shown to accurately recapitulate in vivo observations, a parallel plate flow chamber is used to examine the inhibitory effects of peptides on APL cell line binding and transmigration through endothelium under physiologic flow conditions. Monolayers of endothelial cells are placed in the parallel plate flow chamber, and the leukemic cells are pumped through the chamber at physiologic flow rates. The interaction between the flowing leukemia cells and the endothelium are videotaped microscopically, and the number of rolling, firmly adhered and transmigrated leukemia cells is quantified by computer-assisted image analysis.

With all-trans retinoic acid (ATRA) treatment, the APL cell line NB-4 acquires the ability to firmly attach to activated endothelium via LFA-1/ICAM-1 interaction. Inhibition of LFA-1/ICAM-1 interaction prevents firm adherence to and transmigration through endothelium of the APL cell line under physiologic flow. This has been demonstrated with monoclonal antibodies against LFA-1 and ICAM-1, which prevent firm attachment to and transmigration through activated endothelium of APL cells in a parallel plate flow chamber (Larson et al., 1997; Brown et al., 1999). Flowing ATRA-treated APL cell lines over activated endothelial cell monolayers in a parallel flow chamber determines the effectiveness of peptides to inhibit LFA-1 dependent firm adherence and subsequent transmigration under physiologic flow conditions. ICAM-1 expressed on activated endothelial monolayers are incubated with cyclic peptides over a range of concentrations ($10^{-4}$ to $10^{-8}$ M) and the $IC_{50}$ is determined.

These assays have identified the efficacy of the cyclic peptide inhibitor having the amino acid sequence, CLL-RMRSIC (SEQ ID NO:3). This peptide binds to ICAM-1 and blocks cell-cell adhesion that is dependent on LFA-1 binding to its ligand, ICAM-1 and has an $IC_{50}$ of 800 $\mu$M for cell aggregation and 250 nM for monovalent LFA-1/ICAM-1 binding. In contrast to other peptide inhibitors, this compound has no structural similarity to fragments or portions of LFA-1 or ICAM-1. This compound is, therefore, an effective agent in the treatment of myocardial infarction, rheumatoid arthritis, asthma, and leukemia/lymphoma and is contemplated to be especially effective in adjunct therapy of acute T-ALL and retinoic acid syndrome in APL.

Regarding the clinical utility of the disclosed compositions, preliminary data indicate that approximately 80% of cases of T-ALL may utilize LFA-1 dependent adhesion for survival. Therefore, the peptide inhibitor may be useful in 80% of cases of T-ALL when incorporated as adjunct therapy. Side effects related to use of a small peptide are contemplated to be minimal, since peptidomimetics inhibiting other integrin functions, and now in clinical trial do not have significant side-effects (Ohman et al., 1995; Adgey, 1998). However, LFA-1 may be critical to an aspect of hematopoiesis that is as yet undefined.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adgey, "An Overview of the Results of Clinical Trials With Glycoprotein IIB/IIIa inhibitors," *Amer Heart J* 135:S43, 1998.

Anderson and Springer, "Leukocyte adhesion deficiency: An inherited defect in the Mac1, and p150, 95 glycoproteins," *Ann Rev Med*, 38:175, 1987.

Bargatze et al., "Distinct roles of L-selectin and integrins a4B7 and LFA-1 in lymphocyte homing to Peyer's patch-HEV in situ: the multistep model confirmed and refined," *Immunity*, 3:99, 1995.

Belhadj Jrad and Bahraoui, "Antigenicity of linear and cyclic peptides mimicking the disulfide oops I HIV-2 envelope glycoprotein: synthesis, reoxidation, and purification," *J Peptide Res*, 51:370, 1998.

Brown et al., "All trans retinoic acid differentially regulates adhesion mechanisms and transmigration on the acute promyelocytic cell NB-4 under physiologic flow," *J Clin Invest*. in press (attached)

Brown et al., "All-trans retinoic acid regulates adhesion mechanism and transmigration of the acute promyelocytic leukemia cell line NB-4 under physiologic flow," *Brit. J Haematol.*, 107:86,1999.

Budnik et al., "Analysis of the production of soluble ICAM-1 molecules by human cells," *Exp Hematol*, 24:3 52, 1996.

Carlos and Harlan, "Leukocyte-endothelial adhesion molecules," *Blood*, 84:2068, 1994.

Cavazzana-Calvo et al., prevention of bone marrow and cardiac graft rejection in an H-2 haplotype disparate mouse combination by an anti-LFA-1 antibody," *Transplantation*, 59:1576, 1995.

Ciufetti et al., "Neutorphil-derived adhesion molecules in human digital ischaemia and reperfusion", *Vasa*, 24:155, 1995.

Cosimi et al., In vivo effects of monoclonal antibody to ICAM-1 (CD54) in nonhuman primates with renal allografts," *J. Immunol*, 144:4604, 1990.

Cox, "The Analysis of Binary Data", Methuen, London, 1970.

Cumberbatch et al., "Adhesion molecule expression by epidermal Langerhans cells and lymph node dendritic cells: a comparison," *Arch. Dermatol. Res.*, 288:739, 1996.

Cunningham and Wells, "High-resolution epitope mapping of hHGH-receptor interactions by alanine-scanning mutagenesis," *Science*, 244:1801, 1989.

Cuthbertson et al., "Design of low molecular weight hematoregulatory agents from the structure-activity relationship of a dimeric pentapeptide," *J Medicinal Chem* 40:2876, 1997.

Davies et al., Induction of persistent T cell hyporesponsiveness in vivo by monoclonal antibody to ICAM-1 in patients with rheumatoid arthritis," *J. Immunol.*, 154:3525, 1995.

DeMeester et al., "Attenuation of rat lung isograft reperfusion injury with a combination of anti-ICAM-1 and anti-beta2 integrin monoclonal antibodies," *Transplantation* 62:1477, 1996.

Diamond and Springer, "The dynamic regulation of integrin adhesiveness," *Curr Biol*, 4:506, 1994.

Doyle et al., "Solution structure of a biologically active cyclic LDV peptide analogue containing a type II' β-turn mimetic," Int. *J. peptide Protein Res.* 47:427 (1996).

Endemann et al., "Novel anti-inflammatory compounds prevent CD 1 1b/Cd 18, alpha M beta 2 (mac-1)-dependent neutrophil adhesion without blocking activation-induced changes in Mac-I," *J Pharm & Exp Therap.* 276:5, 1996.

Gerszten et al., "Adhesion of memory lymphocytes to vascular cell adhesion molecule-1 transducted human vascular endothelial cells under simulated physiological flow conditions in vitro," *Circulatory Research* 79:1205, 1996.

Goligorsky et al., "Therapeutic effect of arginine-glycine-aspartic acid peptides in acute renal injury," *Clin Exper Pharm Physiol* 25:276, 1998.

Greenwood et al., "Lymphocyte adhesion and transendothelial. migration in the central nervous system: the role of LFA-1, ICAM-1, VLA-4, and VACM-I," *Immunology* 86:408, 1995.

Gundel et al., "The Role of Intercellular Adhesion Molecule-1 in Chronic Airway Inflammation," *Clin Exp Allergy*, 22:569, 1992.

Hagegawa et al., Prevention of autoimmune insulin-dependent diabetes in non-obese mice by anti-LFA-1 and anti-ICAM-1 mAb," *Int. Immunol.*, 6:831, 1994.

Hamamoto et al., "Impact of adhesion molecules of the selectin family on liver microcirculation at reperfusion following cold ischemia," *Transplant International* 9:454, 1996.

Flaming et al., "Monoclonal antibodies to lymphocyte function-associated antigen-1 inhibit invasion of human lymphoma and metastasis of murine lymphoma," *Clin Exp Metastasis* 11:337, 1993.

Isobe et al., "Specific acceptance of cardiac allograft after treatment with anti-ICAM-1 and anti-LFA-1," *Science*, 255:1125, 1992.

Jackson et al., "Potent alpha 4 beta 1 peptide antagonists as potential anti-inflammatory agents," *J Medicinal Chem* 40:3359,1997.

Jacobsson and Frykberg, "Phage display shot-gun cloning of ligand-binding domains of prokaryotic receptors approaches 100% correct clones," *Biotechniques* 20:1070, 1996.

Johnston et al., "On the species specificity of the interaction of LFA-1 with intercellular adhesion molecules," *J Immunol* 145:1181, 1990.

Jones et al., "A two-step adhesion cascade for T cell/endothelial cell interactions under flow conditions," *J Clin Invest*, 94:2443, 1994.

Kavanaugh et al., "Treatment of refractory rheumatoid arthritis with a monoclonal antibody to intercellular adhesion molecule-1," *Arthritis Rheum.*, 37:992, 1994.

Larson et al., "Retinoic acid induces aggregation of the acute promyelocytic leukemia cell line NB-4 that is mediated by LFA-1 and ICAM-2," *Blood*, 90:2747, 1997.

Larson et al., "Primary structure of the LFA-1 alpha subunit: An integrin with an embedded domain defining a protein superfamily," *J Cell Biol*, 108:703, 1989.

Larson et al., "The subunit specificity of CD11 a/18, CD11b, and CD11c panels of antibodies," in *Leukocyte Typing*, p 566, 1990.

Larson et al., "The leukocyte integrin LFA-1 reconstituted by cDNA transfection in a nonhematopoietic cell line is functionally active and not transiently regulated," *Cell Regul*, 1:359,1990.

Larson and McCurley, "CD4 Predicts Nonlymphocytic Lineage in Acute Leukemia: Insights From Analysis of 125 Cases Using Two-Color Flow Cytometry," *Am J Clin Path*, 104:204, 1995.

Larson and Springer, "The structure and function of leukocyte integrins," *Immunol Rev* 114:181, 1990.

Larson et al., "All-trans retinoic acid induces neutrophil-like adhesion phenotype on acute promyeliocytic cells (abstract)," *Blood* 90(Suppl 1):522a, 1997.

Lawrence et al., "Effect of venous shear stress on CD 18-mediated neutrophil adhesion to cultured endothelium," *Blood* 75:227, 1990.

Lefkovis and Topol, "Platelet glycoprotein IIb/IIIa receptor inhibitors in ischemic heart disease," *Current Opinion Cardiology* 10:420, 1995.

Liesveld et al., "Adhesive interactions of normal and leukemic human CD34+myeloid progenitors: Role of marrow stromal, fibroblasts and cytomatrix components," *Exp Hematol* 19:63, 1991.

Luscinskas et al., "Endothelial-leukocyte adhesion molecule dependent and leukocyte (CD 11 CD 18) dependent mechanisms contribute to polymorphomiclear leukocyte adhesion to cytokine activated human vascular endothelium," *J Immunol* 142:2257, 1989.

Luscinskas et al., "L- and P-selectins, but not CD49d (VLA-4) integrins, mediate monocyte initial attachment to TNF-alpha activated vascular endothelium under flow in vivo," *J Immunol*, 157:326, 1996.

Ma et al., "In vivo treatment with anti-ICAM-1 and anti-LFA-1 antibodies inhibits contact sensitization-induced migration of epidermal Langerhans cells to regional lymph nodes," *Cell Immunol.*, 15:389, 1994

Manabe et al., "Bone marrow-derived stromal cells prevent apoptotic cell death in B-lineage acute lymphoblastic leukemia," *Blood*, 79:2370, 1992.

Manabe et al., "Adhesion-dependent survival of normal and leukemic human B lymphoblasts on bone marrow stromal cells," *Blood* 83:758, 1994.

Marubayashi et al., "Protective effect of monoclonal antibodies to adhesion molecules on rat liver ischemia-reperfusion injury," *Surgery*, 122:45, 1997.

McEver, "Leukocyte interaction mediated by selectins," *Thrombos Hemost*, 66:80, 1990.

McMurray, "Adhesion molecules in autoimmune disease," *Seminars in Arthritis & Rheumatism* 25:215, 1996.

Murayarna et al., "Novel peptide ligands for integrin alpha 6 beta 1 selected from a phage display library," *J Biochemistry*, 120:445, 1996.

Nakakura et al., "Potent and effective prolongation by anti-LFA-1 monoclonal antibody. monotherapy of non-primarily vascularized heart allograft survival in mice without T-cell depletion," *Transplantation*, 55:412, 1993.

Nakano et al., "Efficacy of intraportal injection of anti-ICAM-1 monoclonal antibody against liver cell injury following warm ischernia in the rat," *Am J Surgery*, 170:65, 1995.

Noiri et al., "Cyclic RGD peptides ameliorate ischemic acute renal failure in rats," *Kidney Intl.*, 46:1050, 1994.

Ohman et al., "Early clinical experience with integrelin, an inhibitor of the platelet glycoprotein IIb/IIIa integrin receptor," *Eur Heart J*, 16:50, 1995.

Ojima et al., "Antithrombotic agents: from RGD to peptide mimerics," *Bioorg Med Chem*, 3:337, 1995.

Pasqualini et al., "A peptide isolated from phage display libraries is a structural and functional mimic of an RGD-binding site on integrins," *J Cell Biol*, 13 0:1189, 1995.

Picker and Butcher, "Physiological and molecular mechanisms of lymphocyte homing," *Annu Rev Immunol*, 10:561, 1992.

Ries et al., "Tables and Graphs.", in SEER cancer statistics review, 1973–1991., National Cancer Institute. National Institutes of Health publication, p 94, 1994.

Roecklein and Torak-Storb, "Functionally Distinct Human Marrow Stromal Cell Lines Immortalized by Transduction with the Human Papilloma Virus E6/E7 Genes," *Blood*, 85:97, 1995.

Romer et al., "Lack of in vitro synergy of clinically used antibodies specific for ICAM-1 and LFA-1," *Transplant Immunol*, 5:162, 1997.

Talento et al., "A single adminsitration of LFA-1 antibody confers prolonged allograft survival," *Transplantation*, 55:418, 1993.

Servilje et al., "Changes in T-cell phenotype and adhesion molecules expression in psoriatic lesions after lose-dose cyclosporin therapy," *J Cutan. Pathol.*, 23:431, 1996.

Springer, "Traffic signals of lymphocyte recirculation and leukocyte emigration: the multistep paradigm," *Cell*, 76:301, 1994.

Staunton et al., "The arrangement of the immunoglobulin-like domains of ICAM-1 and the binding sites for LFA-1 and rhinovirus," *Cell*, 61:243, 1990.

Stepkowski et al., "Blocking of heart allograft rejection by intercellular adhesion molecule-I antisense oilgonucelotides alone or in combination with other immunosuppressive modalities," *J Immunol.*, 144:4604, 1990.

Suehiro et al., "The ligand recognition specificity of beta3 integrins," *J Biol Chem*, 271: 10365, 1996.

Tallman et al., "All-trans-retinoic acid in acute promyelocytic leukemia," *N Eng J Med*, 337:1021, 1997.

Tibbets et al., "Peptides derived from ICAM-1 and LFA-1 modulate T cell adhesion and immune function in a mixed lymphocyte culture," *Transplantation*, 68:685, 1999.

Van der Vieren et al., "A novel leukointegrin, alpha d beta 2, binds preferentially to ICAM-3," *Immunity*, 3:683, 1995.

Vanderslice et al., "A cyclic hexapeptide is a potent antagonist of alpha4 integrins," *J Immunol*, 158:1710, 1997.

Wang et al., "Epstein-Barr virus latent infection membrane (LMP) protein alters lymphocyte morphology, adhesion, and growth: Deletion of the amino terminus abolishes activity," *J Virol* 62:4173, 1988.

Winter et al., "Combinatorial effects of LFA-1 dependent stromal cell adherence and soluble factor(s) on T-ALL cell survival (abstract)," *Blood*, 89 (suppl 1):81a, 1998.

Zhang and Plow, "A discrete site modulates activation of I domains. Application to integrin alpha Mbeta2," *J Biol Chem*, 271:29953, 1996.

What is claimed is:

1. A composition comprising a cyclic peptide inhibitor of LFA-1/ICAM-1 interaction, wherein the cyclic peptide has the amino acid sequence of SEQ ID NO:3, or a substitution of SEQ ID NO:3 wherein the $2^{nd}$ amino acid is methionine, the $5^{th}$ amino acid is proline, the $6^{th}$ amino acid is asparagine, the $7^{th}$ amino acid is leucine, or the $8^{th}$ amino acid is arginine, or a conservative variant of any thereof.

2. The composition of claim 1, wherein the $2^{nd}$ amino acid in said amino acid sequence is methionine.

3. The composition of claim 1, wherein the $5^{th}$ amino acid in said amino acid sequence is proline.

4. The composition of claim 1, wherein the $6^{th}$ amino acid in said amino acid sequence is asparagine.

5. The composition of claim 1, wherein the $7^{th}$ amino acid in said amino acid sequence is leucine.

6. The composition of claim 1, wherein the $8^{th}$ amino acid in said amino acid sequence is arginine.

7. The composition of claim 1, wherein the $2^{nd}$ amino acid is either leucine or methionine, the $5^{th}$ amino acid is either methionine or proline, the $6^{th}$ amino acid is either arginine or asparagine, the $7^{th}$ amino acid is either serine or leucine, and the $8^{th}$ amino acid is either isoleucine or arginine.

8. The composition of claim 1, wherein said composition is contained in a pharmaceutically acceptable carrier.

9. The composition of claim 1, wherein said composition exhibits an $IC_{50}$ of cell aggregation mediated by LFA-1/ICAM-1 binding of from about 10 μM to about 850 μM.

10. The composition of claim 1, wherein said composition exhibits an $IC_{50}$ of monovalent LFA-1/ICAM-1 of from about 10 nM to about 250 nM.

11. A method of inhibiting in a subject the interaction between LFA-1 expressed on a leukocyte and ICAM-1 expressed on a second cell, comprising administering to said subject an effective amount of a composition comprising a cyclic peptide, wherein said cyclic peptide has the amino acid sequence of SEQ ID NO:3 or a conservative variant thereof.

12. The method of claim 11, wherein said second cell is an bone marrow stromal cell.

13. The method of claim 11, wherein said second cell is an endothelial cell.

14. A method of preventing retinoic acid syndrome in a subject receiving a retinoic acid, 9-cis-retinoic acid, or a synthetic retinoid that causes or is suspected of causing retinoic acid syndrome when administered to a subject, comprising administering to said subject an effective amount of a composition comprising a cyclic peptide, wherein said peptide has the amino acid sequence of SEQ ID NO:3 or a conservative variant thereof.

15. A method for inhibiting growth of leukemia cells comprising preventing an LFA-1/ICAM-1 interaction between said leukemia cells and bone marrow stromal cells, wherein said method comprises contacting said bone marrow stromal cells with a cyclic peptide inhibitor of said LFA-1/ICAM-1 interaction, and further wherein the amino acid sequence of said cyclic peptide inhibitor is not a fragment of the amino acid sequence of LFA-1 or ICAM-1.

16. The method of claim 15, wherein said leukemia cells are in a leukemia patient and said contacting comprises administering said cyclic peptide to said patient.

17. The method of claim 15, wherein said cyclic peptide inhibitor has the sequence of SEQ ID NO:3 or a conservative variant thereof.

18. A therapeutic package for dispensing to, or for use in dispensing to, a mammal being treated for a hematopoietic neoplastic disease, myocardial infarction, radiation injury, asthma, rheumatoid arthritis, or lymphoma metastasis, wherein said package contains in a unit dose, an amount of a cyclic peptide having the amino acid sequence of SEQ ID NO:3 or a conservative variant thereof, effective to inhibit an LFA-1/ICAM-1 interaction in said mammal when administered periodically.

19. The package of claim 18, wherein said package is formulated for intravenous administration.

20. The package of claim 18, wherein said package includes said unit dose in a dry powder form.

21. The package of claim 18, wherein said unit dose will deliver a dose from about 10 µg/Kg to about 500 µg/Kg.

22. The package of claim 18, wherein said unit dose will deliver a dose from about 50 µg/Kg to about 250 µg/Kg.

23. A composition comprising a cyclic peptide inhibitor of LFA-1/ICAM-1 interaction, wherein said cyclic peptide has the amino acid sequence of SEQ ID NO:3.

24. A method of inhibiting emigration of leukocytes from blood into tissue in a subject comprising administering to said subject an amount of a cyclic peptide having the amino acid sequence of SEQ ID NO:3 or a conservative variant thereof, effective to inhibit an LFA-1/ICAM-1 interaction in said subject.

25. The method of claim 24, wherein said cyclic peptide has the amino acid sequence of SEQ ID NO:3.

26. The method of claim 24, wherein said subject is susceptible to the development of or is suffering from a hematopoietic neoplastic disease, myocardial infarction, radiation injury, asthma, rheumatoid arthritis, or lymphoma metastasis.

27. A method of screening a candidate compound for binding to ICAM-1 comprising:

(a) contacting ICAM-1 with a peptide having the amino acid sequence of SEQ ID NO:3 or a conservative variant thereof, such that said peptide having the amino acid sequence of SEQ ID NO:3 or a conservative variant thereof, is bound to the ICAM-1:

(b) contacting said ICAM-1 with said bound peptide having the amino acid sequence of SEQ ID NO:3 or a conservative variant thereof, with said candidate compound; and (c) quantifying displaced peptide having the amino acid sequence of SEQ ID NO:3 or a conservative variant thereof.

28. The method of claim 27, wherein said cyclic peptide having the amino acid sequence of SEQ ID NO:3, or a conservative variant thereof, is radiolabeled.

29. The method of claim 27, wherein said cyclic peptide having the amino acid sequence of SEQ ID NO:3, or a conservative variant thereof, is labelled with a flurophore.

30. The composition of claim 1, wherein the cyclic peptide has the amino acid sequence of SEQ ID NO:3.

* * * * *